US012799466B2

(12) United States Patent
Pérez Jiménez et al.

(10) Patent No.: US 12,799,466 B2
(45) Date of Patent: Nov. 17, 2026

(54) SYNTHETIC PRIMASE-POLYMERASE AND USES THEREOF

(71) Applicant: TYRIS THERAPEUTICS, S.L., Paterna (ES)

(72) Inventors: Raúl Pérez Jiménez, Donostia (ES); Ane Quesada Ganuza, Donostia (ES); Borja Alonso Lerma, Donostia (ES); Julen Oyarzabal Santamarina, Madrid (ES)

(73) Assignee: TYRIS THERAPEUTICS, S.L., Paterna (ES)

( * ) Notice: Subject to any disclaimer, the term of this patent is extended or adjusted under 35 U.S.C. 154(b) by 0 days.

(21) Appl. No.: 19/552,205

(22) Filed: Feb. 27, 2026

(65) Prior Publication Data

US 2026/0176600 A1 Jun. 25, 2026

Related U.S. Application Data

(63) Continuation of application No. 18/879,210, filed as application No. PCT/EP2023/067649 on Jun. 28, 2023.

(30) Foreign Application Priority Data

Jun. 29, 2022 (EP) .................................... 22382615

(51) Int. Cl.
*C12N 9/12* (2006.01)
*C12P 19/34* (2006.01)
(Continued)

(52) U.S. Cl.
CPC ......... *C12N 9/1241* (2013.01); *C12N 9/1252* (2013.01); *C12P 19/34* (2013.01);
(Continued)

(58) Field of Classification Search
None
See application file for complete search history.

(56) References Cited

U.S. PATENT DOCUMENTS 9,109,250 B2 8/2015 Hill
11,299,718 B2 * 4/2022 Picher .................... C12Q 1/686
(Continued)

FOREIGN PATENT DOCUMENTS

EP 1859812 A1 11/2007
WO 2009100309 A 8/2009
(Continued)

OTHER PUBLICATIONS

"RecName: Full=Prim-Pol domain-containing protein {ECO:0000259|SMART:SM00943}," UniProt Jan. 19, 2022, retrieved from EBI accession No. UNIPROT: A0A8D6L8P0, Database accession No. A0A8D6L8P0.
(Continued)

*Primary Examiner* — Aaron A Priest
(74) *Attorney, Agent, or Firm* — Squire Patton Boggs (US) LLP

(57) ABSTRACT

The present invention provides a polypeptide comprising a sequence selected from the group consisting of SEQ ID NO: 1, SEQ ID NO: 2, and SEQ ID NO: 3, or a variant thereof at least 90% identical to SEQ ID NO: 1, SEQ ID NO: 2, or SEQ ID NO: 3. The invention also provides an antibody that binds to the polypeptide, a nucleic acid molecule encoding the polypeptide, a process for producing the polypeptide, a process for amplifying a nucleic acid, a process for producing closed linear DNA, and a kit comprising the polypeptide.

16 Claims, 4 Drawing Sheets

Specification includes a Sequence Listing.

(51) Int. Cl.
*C12Q 1/6853* (2018.01)
*C12Q 1/6869* (2018.01)

(52) U.S. Cl.
CPC ......... *C12Q 1/6853* (2013.01); *C12Q 1/6869* (2013.01); *C12Y 207/07007* (2013.01)

(56) References Cited

U.S. PATENT DOCUMENTS

| | | | | |
|---|---|---|---|---|
| 12,188,084 B2* | 1/2025 | He | ........................ | C12Q 1/6806 |
| 12,522,864 B2 | 1/2026 | Santamarina | | |
| 2020/0362403 A1 | 11/2020 | Serantes | | |
| 2022/0235337 A1* | 7/2022 | Picher Serantes | ... | C12N 9/1252 |

FOREIGN PATENT DOCUMENTS

| | | |
|---|---|---|
| WO | 2011000997 A1 | 1/2011 |
| WO | 2014140309 A1 | 9/2014 |
| WO | 2019101596 A1 | 5/2019 |
| WO | 2021152146 A1 | 8/2021 |

OTHER PUBLICATIONS

"SubName: Full=Bifunctional DNA primase/polymerase famiily protein {ECO:0000313|EMBL:AFV75132.1};", UniProt Feb. 6, 2013, retrieved from EBI accession No. UNIPROT: K7REW6, Database accession No. K7REW6.

Picher et al., "TruePrime is a novel method for whole-genome amplification from single cells based on TthPrimPol", Nature Communications, vol. 7, No. 1, Dec. 1, 2016, URL:https://www.nature.com/articles/ncomms13296.pdf DOI: 10.1038/ncomms13296.

Macaulay et al., "Single Cell Genomics: Advances and Future Perspectives", PLOS Genetics, vol. 10, No. 1, Jan. 30, 2014, p. e1004126, DOI: 10.1371/journal.pgen.1004126.

Altschul et al., "Basic local alignment search tool", J. Mol. Biol, 1990, v. 215, pp. 403-410.

Guilliam et al., "Human PrimPol is a highly error-prone polymerase regulated by single-stranded DNA binding proteins", Nucleic Acids Res, Jan. 2015, vol. 43(2), pp. 1056-1068.

Heinrich et al., "Linear closed mini DNA generated by the prokaryotic cleaving-joining enzyme TelN is functional in mammalian cells", J Mol Med, 2002, vol. 80(10), pp. 648-654.

PCT International Search Report and Written Opinion of the International Searching Authority dated Jul. 11, 2023, PCT Patent Application No. PCT/EP2023/067469.

Xiao, et al., "A novel 165-base-pair terminal repeat sequence is the sole cis requirement for the adeno-associated virus life cycle", Journal of Viralogy; Feb. 1997; vol. 71(2), pp. 941-948.

PTO-892 issued in U.S. Appl. No. 19/421,128 on Jul. 29, 2026, 1 page.

SB-429 filed in U.S. Appl. No. 19/421,128 on Jul. 16, 2026, 2 pages.

Xiao, et al., "A novel 615-base pair terminal repeat sequence is the sole cis requirement for the adeno-associated virus life cycle", Journal of Viralogy; Feb. 1997; vol. 71(2), pp. 941-948.

* cited by examiner

SYNTHETIC PRIMASE-POLYMERASE AND USES THEREOF

CROSS-REFERENCE TO RELATED APPLICATION(S)

The present application is a continuation application of U.S. patent application Ser. No. 18/879,210, filed Dec. 26, 2024, which is a national phase filing under 35 U.S.C. § 371 of International Application No. PCT/EP2023/067649, filed on Jun. 28, 2023, which claims the benefit of European Patent Application EP22382615 filed on Jun. 29, 2022, all of which are incorporated herein by reference in their entireties.

INCORPORATION BY REFERENCE

This application includes an electronically submitted sequence listing in xml format. The xml file contains a sequence listing entitled "P6012PC00_filing_sequence_listing_20230626_. xml" which is dated Jul. 1, 2023, and is 7,626 bytes in size. The sequence listing contained in this xml file is part of the specification and is herein incorporated by reference in its entirety.

TECHNICAL FIELD

The present invention relates to the field of molecular biology. More particularly, it relates to synthetic primase-polymerases (PrimPols) particularly useful for priming the amplification of nucleic acid templates.

BACKGROUND ART

The introduction of in vitro nucleic acid amplification techniques has revolutionized the fields of biomedical research, disease diagnosis, and forensics. More recently, these techniques have also become an essential tool for the large production of nucleic acids for therapy, such as gene therapy products.

Unfortunately, in vitro nucleic acid amplification is a process inherently subjected to bias, error, and co-amplification of residual levels of contaminating nucleic acids. A major source of potential amplification problems in current methods arises from the use of primers. Primers are short oligonucleotides that provide the starting point that DNA polymerases need for DNA synthesis. However, primers have a strong propensity to generate primer-derived artefacts and often lead to amplification inequality generated by different sequence-dependent hybridization kinetics.

Not surprisingly, the development of amplification systems that do not rely on the use of primers has been the object of strong research in recent years. Several primase-based methods have been recently developed in order to avoid the problems derived from using oligonucleotide-based priming.

Primase-polymerases (PrimPols) are a class of enzymes that have been used in amplification methods given their compatibility with highly processive DNA polymerases such as Phi29 polymerase, Most efforts made so far have been focused on identifying existing bacterial and archaeal PrimPols that could improve current amplification methods. However, natural PrimPols identified until now have limited efficiency under industrial conditions, such as low pH or high temperatures, which strongly hinders their use in industrial settings.

Thus, there is still a need in the art for improved PrimPols that can be used under industrial conditions for efficiently amplifying nucleic acids.

SUMMARY OF INVENTION

The present inventors have developed various synthetic primase-polymerase enzymes (PrimPols) particularly useful for nucleic acid-amplification processes.

As shown in the Examples below, the synthetic PrimPols developed by the inventors surprisingly provide various advantages over natural PrimPols that make them particularly suitable for their application in industrial processes. For example, synthetic PrimPols have higher expression rates than natural PrimPols, and also provide higher nucleic acid amplification yields under certain conditions—such as lower pH and higher temperatures—while maintaining a very high sequence fidelity. Advantageously, synthetic PrimPols herein provided are compatible with highly processive strand-displacement DNA polymerases, which allows their combined use to generate very large quantities of high-quality nucleic acids.

All these unique characteristics make the synthetic PrimPols of the invention important molecular tools for any application that involves the amplification of nucleic acids, especially in industrial settings.

Thus, in a first aspect, the invention provides a polypeptide comprising a sequence selected from the group consisting of SEQ ID NO: 1, SEQ ID NO: 2, and SEQ ID NO: 3, or a variant thereof at least 80% identical, particularly at least 90% identical, to SEQ ID NO: 1, SEQ ID NO: 2, or SEQ ID NO: 3.

In a second aspect, the invention provides an antibody that specifically binds to a polypeptide comprising or consisting of a sequence selected from the group consisting of SEQ ID NO: 1, SEQ ID NO: 2, and SEQ ID NO: 3.

In a third aspect, the invention provides a nucleic acid sequence that encodes the polypeptide as defined in the first aspect, particularly, wherein the nucleic acid sequence is optimized for expression in a mammalian expression system, or alternatively, in a bacterial expression system.

In a fourth aspect, the invention provides a gene construct comprising a nucleic acid sequence as defined in the third aspect operatively linked to an expression promoter.

In a fifth aspect, the invention provides an expression vector comprising the gene construct as defined in the fourth aspect.

In a sixth aspect, the invention provides a host cell comprising the nucleic acid sequence as defined in the third aspect, the gene construct as defined in the fourth aspect, or the expression vector as defined in the fifth aspect.

In a seventh aspect, the invention provides a process for producing the polypeptide as defined in the first aspect, the process comprising the steps of a) culturing the host cell as defined in the sixth aspect under conditions suitable for the production of the polypeptide; b) recovering the polypeptide; and, optionally, c) purifying the polypeptide.

In an eighth aspect, the invention provides a polypeptide obtainable by the process defined in the seventh aspect.

In a ninth aspect, the invention provides a process for amplifying a nucleic acid that comprises the step of contacting the nucleic acid with a polypeptide as defined in the first aspect; and optionally, a DNA polymerase, particularly a strand-displacement DNA polymerase; under conditions suitable for amplifying the nucleic acid.

In a tenth aspect, the invention provides the use of a polypeptide as defined in the first aspect for amplifying, detecting, or sequencing a nucleic acid.

In an eleventh aspect, the invention provides the use of a polypeptide as defined in the first aspect in combination with a DNA polymerase, particularly a strand-displacement DNA polymerase, for amplifying, detecting, or sequencing a nucleic acid.

In a twelfth aspect, the invention provides a process for the production of a closed linear DNA comprising the steps of a) providing a DNA template comprising a DNA sequence of interest; b) amplifying DNA from the DNA template of step (a) wherein the amplification is primed with a polypeptide as defined in the first aspect; c) generating a closed linear DNA with the amplified DNA produced in step (b); and d) optionally, purifying the generated closed linear DNA.

In a thirteenth aspect, the invention provides the use of a polypeptide as defined in the first aspect for the production of closed linear DNA.

In a fourteenth aspect, the invention provides a kit comprising a) a polypeptide as defined in the first aspect; b) a DNA polymerase, particularly, a strand-displacement DNA polymerase; and c) optionally, instructions for its use.

DETAILED DESCRIPTION OF THE INVENTION

Figure 1:
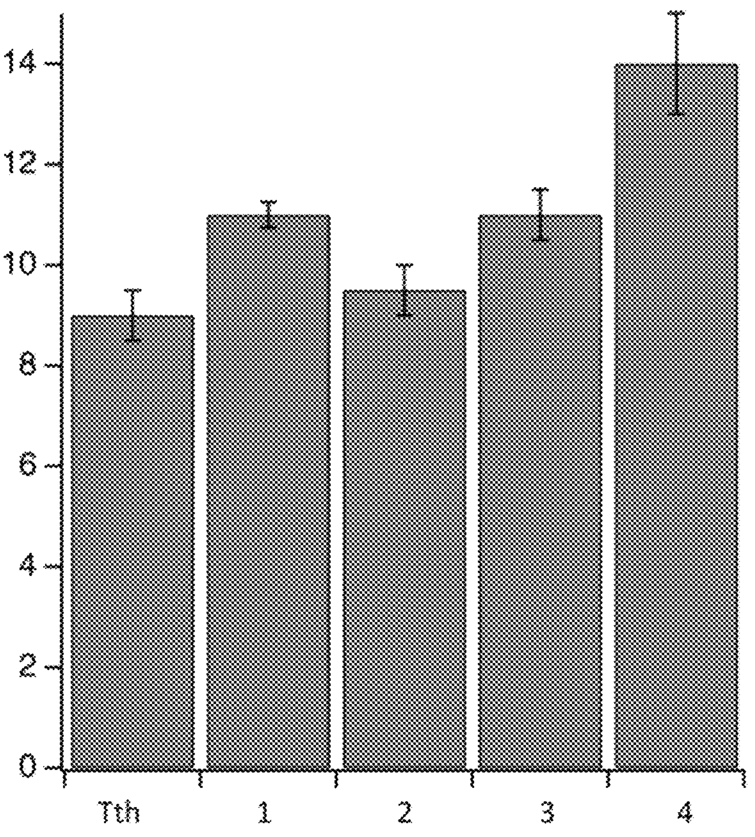
FIG. 1, related to Example 2, shows the expression rates of synthetic PrimPols and TthPrimPol. The y-axis represents the amount of enzyme (mg) produced per bacterial culture liter as determined by absorbance measurements at 280 nm. "Tth" refers to TthPrimPol; "1" refers to PrimPol 1 of SEQ ID NO:1; "2" refers to PrimPol 2 of SEQ ID NO: 4; "3" refers to PrimPol 3 of SEQ ID NO:3; and "4" refers to PrimPol 4 of SEQ ID NO: 2.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

For purposes of the present invention, any ranges given include both the lower and the upper end-points of the range. Ranges given, such as concentrations and the like, should be considered approximate, unless specifically stated. The term "about" refers to a deviation of plus/minus 10%, preferably plus/minus 5%.

As above described, in a first aspect the invention provides a polypeptide comprising a sequence selected from the group consisting of SEQ ID NO: 1, SEQ ID NO: 2, and SEQ ID NO: 3, or a variant thereof at least 80% identical, particularly at least 90% identical, to SEQ ID NO: 1, SEQ ID NO: 2, or SEQ ID NO: 3. Thus, this aspect is meant to be directed to a polypeptide comprising sequence SEQ ID NO: 1 or a variant thereof at least 80% identical, particularly at least 90% identical, to SEQ ID NO: 1; a polypeptide comprising sequence SEQ ID NO: 2 or a variant thereof at least 80% identical, particularly at least 90% identical, to SEQ ID NO: 2, and a polypeptide comprising sequence SEQ ID NO: 3 or a variant thereof at least 80% identical, particularly at least 90% identical, to SEQ ID NO: 3. The invention also provides a polypeptide comprising a sequence at least 80% identical, particularly at least 90% identical, to SEQ ID NO:1, SEQ ID NO:2, or SEQ ID NO: 3.

Sequences SEQ ID NO: 1 to 4 are disclosed in Table 1 below:

TABLE 1

| SEQ ID | Name | Sequence |
|---|---|---|
| SEQ ID NO: 1 | PrimPol 1 | RAPHSSPLEAALGYARLGYPVLPLLPGEKRPHPRLV<br>PHGLKEASQDPATLEAWWRSCPEAGVGILAPAGVL<br>VLDFDDPTAWEGLRQEHPALEAAPRQRTPKGGVHV<br>FLRLPEGVRLSASVRAIPGVDLRGMGRAYVVAAPTR<br>LKDGRTYSWEVPLVRPAELPPVPEALLARLLPPPPP<br>PPREVWTPVEGASPKRLRALLEAYAHRVAATPPGT<br>RHNTLIRYAVAAGGLIPHGLDPREAEEALVAAALSAG<br>LPEREARAAVRWGLEVGRSRPLDLESSLPPRLPWT<br>YRGRVYARVRRWA |
| SEQ ID NO: 2 | PrimPol 4 | AHSTSPLEAALGYARMGYPVLPVAPGSKRPHPRLV<br>PHGLKEASTDPATIEAWWRSCPEANVGILAPEGVLV<br>LDLDDPTAWEGLRQLHPALLAAPRARTPRGGVHLY<br>LRLPPGVRLSASVRALPGVDLRGMGRAYVVAAPSR<br>LKDGRTYAWVVPLRRPSELPPVPQALLARLLAPPPP<br>PAARPVSTPVEGASPKRLRALLEAACHRVAHTPPG<br>QRHNTLIRHAVAVGGLIPHGLDQEEAEEALVAAALS<br>AGLPEREARAAVRWGLEAGASRPLVLKPSLPPRLR<br>WTIRRRVRARGRRHG |
| SEQ ID NO: 3 | PrimPol 3 | ALSTSPLEAALGYARMGYPVLPVAPGSKRPHPRLV<br>RHGLKEATTDPALIEAWWSSRPEANVGILPPAGVLV<br>LDLDSPAGWAGLRQLHPALLAAPRARTPGGGVHLY<br>FRLPPGVRLSASVRVLPGVDLRGMGRAYVVAPPSR<br>HADGRTYEWVVPLRRPSELPPVPQALLALLLAPPPP<br>PAARPVSTPVASARPKAYRAALEAECDRVARTPPG<br>QRHNTLIRHAVALGGLIPRGLDQEEVEGALLAAALR<br>AGLPEREARAAIRWGLEAGASRPLALKPRLPPRLR<br>WTIRRRARARGRRHG |
| SEQ ID NO: 4 | PrimPol 2 | ALSTSPLEAALAYARMGYPVLPVAPGSKRPHPRLVR<br>HGLKEATTDPAQIEAWWSRRPEANVGILTPSGVLVL<br>DLDSPDGWAGLRQLHPALLPAPKVRTPGGGVHLYF<br>RLPPGVRLRASVRVLPGIDLRGMGRAYVVAPPSRH<br>AHGRTYEWVVPLRAPSELPPVPQALLALLLAPPPPP<br>AARPVSPPVASARPDAYRAALEAECDRVARTPPGQ<br>RHNTLIRHAVALGGLVPRGLDEEEVEGALLAAALRA<br>GLAEREARATIRWGLEAGASRPLDLRPRLPPRLRW<br>RIRRRARARGRRHG |

Polypeptide sequence variants are well understood to those of skill in the art and can involve amino acid sequence modifications. For example, amino acid sequence modifications typically fall into one or more of three classes: substitutional, insertional, or deletional variants.

In the present invention the term "identical" or "identity" refers to the percentage of residues that are identical in the two sequences when the sequences are optimally aligned. If, in the optimal alignment, a position in a first sequence is occupied by the same amino acid residue as the corresponding position in the second sequence, the sequences exhibit identity with respect to that position. The percentage of identity determines the number of identical residues over a defined length in a given alignment. Thus, the level of identity between two sequences or ("percent sequence identity") is measured as a ratio of the number of identical positions shared by the sequences with respect to the number of positions compared (i.e., percent sequence identity=(number of identical positions/total number of positions compared)×100). A gap, i.e., a position in an alignment where a residue is present in one sequence but not in the other, is regarded as a position with non-identical residues and is counted as a compared position.

As an illustration, by a polypeptide having an amino acid sequence being at least, for example, 95% identical to a reference amino acid sequence of SEQ ID NO:1 is intended that the amino acid sequence of the polypeptide is identical to the reference sequence except that the polypeptide sequence may include up to five amino acid alterations per each 100 amino acids of the reference amino acid of SEQ ID NO: 1. In other words, to obtain a polypeptide having an amino acid sequence of at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

A number of mathematical algorithms for rapidly obtaining the optimal alignment and calculating identity between two or more sequences are known and incorporated into a number of available software programs. For purposes of the present invention, the sequence identity between two amino acid sequences is preferably determined using algorithms based on global alignment, such as the Needleman-Wunsch algorithm (Needleman and Wunsch, 1970, J. Mol. Biol. 48:443-453), preferably implemented in the Needle program of the EMBOSS package (EMBOSS: The European Molecular Biology Open Software Suite, Rice et al., 2000, Trends Genet. 16:276-277); or the BLAST Global Alignment tool (Altschul et al., "Basic local alignment search tool", 1990, J. Mol. Biol, v. 215, pages 403-410), using default settings. Local alignment also can be used when the sequences being compared are substantially the same length.

In a particular embodiment of the first aspect, optionally in combination with any of the embodiments provided above or below, the polypeptide comprises primase and polymerase activities (i.e., the polypeptide is a primase-polymerase or PrimPol). In a more particular embodiment, the polypeptide comprises DNA primase and DNA polymerase activities. The skilled person would know how to test whether a polypeptide comprises primase and polymerase activities using its common general knowledge; for example, the polypeptide could be contacted with a nucleic acid under conditions suitable for amplification and the reaction products could then be measured by absorbance at a wavelength of 260 nm.

In a particular embodiment of the first aspect, optionally in combination with any of the embodiments provided above or below, the polypeptide comprises at least one improved property as compared to TthPrimPol.

As used herein, the term "primase-polymerase" is used interchangeably with "PrimPol" and refers to a group of enzymes that have both primase and polymerase activities. The term "TthPrimPol" is well known to the skilled person and refers to *Thermus thermophilus* HB27 primase-polymerase, which is described, for example, in WO2019101596 (FIG. 18, SEQ ID NO: 10). It bears Gene ID: NC_005835 in the NCBI Entrez database, protein WP_01 1173100.1 TthPrimPol can be obtained commercially.

In a particular embodiment of the first aspect, optionally in combination with any of the embodiments provided above or below, the at least one improved property as compared to TthPrimPol is selected from greater pH stability, greater thermostability, greater primase activity, greater polymerase activity, greater fidelity, and greater expression rate. In a particular embodiment, the polypeptide comprises greater primase activity than TthPrimPol at pH 7.5. In a more particular embodiment, the polypeptide comprises greater primase and/or polymerase activity than TthPrimPol, particularly at a pH of about 7.5. In another particular embodiment, the polypeptide comprises greater primase and/or polymerase activity than TthPrimPol, particularly at a temperature of about 50° C. In an even more particular embodiment, the polypeptide comprises a greater primase and/or polymerase activity than TthPrimPol, particularly at a pH of about 7.5 and a temperature of about 50° C.

Primase and polymerase activities can be measured by routine methods well known to the skilled in the art, for instance, by the methods disclosed in the Examples below. In a particular embodiment, the primase or polymerase activity is measured by a method selected form the group consisting of absorbance at a wavelength of 260 nm, in situ hybridization, reverse-transcriptase polymerase chain reaction, nucleic acid hybridization, electrophoresis, Southern blotting and mass spectrometry. In a more particular embodiment, the primase or polymerase activity is measured by absorbance at a wavelength of 260 nm.

In a more particular embodiment, the primase activity is measured by contacting the polypeptide of the invention and a strand-displacement DNA polymerase, particularly, a Phi29 polymerase, with a nucleic acid template under conditions suitable for amplifying the nucleic acid template and measuring the amplification products by absorbance at a wavelength of 260 nm. A higher primase activity of the polypeptide would result in a higher amount of amplification product produced by the DNA polymerase. The conditions suitable for amplifying the nucleic acid template with the polypeptide and the strand-displacement DNA polymerase are well known to the skilled person. These conditions may be, for instance, the conditions disclosed in Example 1 below.

In another particular embodiment, the polymerase activity is measured by contacting the polypeptide with a nucleic acid template under conditions suitable for amplifying the nucleic acid template and measuring the amplification products by absorbance at a wavelength of 260 nm. The conditions suitable for amplifying the nucleic acid template with the polypeptide are well known to the skilled person. These conditions may be, for instance, the conditions disclosed in the Examples below.

The term "fidelity" refers to the accuracy of template-directed incorporation of complementary bases in a synthesized nucleic acid strand relative to the template strand. Fidelity may be measured based on the frequency of incorporation of incorrect bases in the newly-synthesized nucleic acid strand. The incorporation of incorrect bases may result in point mutations, insertions or deletions. Methods for determining fidelity are well known in the art. Increased fidelity can be determined by assaying the natural and synthetic PrimPol and comparing their activities using any assay that measures the accuracy of template directed incorporation of complementary bases, such as next-generation sequencing. Such methods are known to those skilled in the art. Thus, in a particular embodiment of the first aspect, fidelity is measured by next-generation sequencing (i.e., by analyzing the sequence of the amplified nucleic acid by next-generation sequencing and determining the frequency of incorporation of incorrect bases).

In a particular embodiment of the first aspect, optionally in combination with any of the embodiments provided above or below, the expression rate is measured by a method selected from the group consisting of absorbance at a wavelength of 280 nm, immunoassay, Western blots, ELISA and mass spectrometry. More particularly, expression rate is measured by absorbance at a wavelength of 280 nm.

In a particular embodiment of the first aspect, optionally in combination with any of the embodiments provided above or below, the variant thereof substantially maintains or improves the primase and polymerase activities. As used herein, by "substantially maintains or improves the primase and polymerase activities" is meant that the variant thereof has at least 90%, more particularly at least 95%, or even more particularly at least 99% of the primase and polymerase activities of the reference polypeptide, measured by any suitable method known in the art, particularly the methods disclosed above. In another particular embodiment, the variant thereof substantially maintains or improves the primase or polymerase activities.

In a particular embodiment of the first aspect, optionally in combination with any of the embodiments provided above or below, the sequence of the polypeptide has an RMS value when aligned against the sequence of TthPrimPol of at least 2, at least 3, at least 4, or at least 5; optionally, wherein the RMS value is calculated with AlphaFold2, particularly, as explained in Example 9.

In a particular embodiment of the first aspect, optionally in combination with any of the embodiments provided above or below, the polypeptide comprises a sequence selected from the group consisting of SEQ ID NO: 1, SEQ ID NO: 2, and SEQ ID NO: 3, or a variant thereof at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 1, SEQ ID NO: 2, or SEQ ID NO: 3, particularly, wherein the variant thereof substantially maintains or improves the primase and polymerase activities.

In a particular embodiment of the first aspect, optionally in combination with any of the embodiments provided above or below, the polypeptide comprises a sequence selected from the group consisting of SEQ ID NO: 1, SEQ ID NO: 2, and SEQ ID NO: 3, or a variant thereof at least 80% identical to SEQ ID NO: 1, SEQ ID NO: 2, or SEQ ID NO: 3, particularly, where the variant thereof has a length of at least 200 amino acids, at least 250 amino acids, at least 280 amino acids, at least 298 amino acids, or about 298 amino acids.

In a particular embodiment of the first aspect, optionally in combination with any of the embodiments provided above or below, the polypeptide comprises the sequence SEQ ID NO: 1 or a variant thereof at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 1, particularly, wherein the variant thereof substantially maintains or improves the primase and/or polymerase activities.

In a particular embodiment of the first aspect, optionally in combination with any of the embodiments provided above or below, the polypeptide comprises the sequence SEQ ID NO: 2 or a variant thereof at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 2, particularly, wherein the variant thereof substantially maintains or improves the primase and/or polymerase activities.

In a particular embodiment of the first aspect, optionally in combination with any of the embodiments provided above or below, the polypeptide comprises the sequence SEQ ID NO: 3 or a variant thereof at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 3, particularly, wherein the variant thereof substantially maintains or improves the primase and/or polymerase activities.

In a particular embodiment of the first aspect, optionally in combination with any of the embodiments provided above or below, the sequence of the polypeptides is not 100% identical to the sequence of any extant polypeptide. In an even more particular embodiment, the sequence of the polypeptide is a synthetic sequence (i.e., a non-naturally occurring sequence). As used herein, the term "extant" refers to taxa (such as species, genera or families) that are still in existence (living). The term extant contrasts with extinct. As used herein, the term "extant polypeptide" refers to polypeptides from extant taxa.

In a particular embodiment of the first aspect, optionally in combination with any of the embodiments provided above or below, the polypeptide consists of a sequence selected from the group consisting of SEQ ID NO: 1, SEQ ID NO: 2, and SEQ ID NO: 3, or a variant thereof at least 80% identical, particularly at least 90% identical, to SEQ ID NO: 1, SEQ ID NO: 2, or SEQ ID NO: 3. Thus, this embodiment is meant to encompass a polypeptide consisting of the sequence SEQ ID NO: 1 or a variant thereof at least 80% identical, particularly at least 90% identical, to SEQ ID NO: 1; a polypeptide consisting of the sequence SEQ ID NO: 2 or a variant thereof at least 80% identical, particularly at least 90% identical, to SEQ ID NO: 2, and a polypeptide consisting the sequence SEQ ID NO: 3 or a variant thereof at least 80% identical, particularly at least 90% identical, to SEQ ID NO: 3.

In a particular embodiment of the first aspect, optionally in combination with any of the embodiments provided above or below, the polypeptide consists of sequence SEQ ID NO: 1 or a variant thereof consisting of a sequence at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 1.

In a particular embodiment of the first aspect, optionally in combination with any of the embodiments provided above or below, the polypeptide consists of sequence SEQ ID NO: 2 or a variant thereof consisting of a sequence at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 2.

In a particular embodiment of the first aspect, optionally in combination with any of the embodiments provided above or below, the polypeptide consists of sequence SEQ ID NO: 3 or a variant thereof consisting of a sequence at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 3.

In one embodiment, the polypeptide comprises a sequence selected from the group consisting of SEQ ID NO: 1, SEQ ID NO: 2, and SEQ ID NO: 3, or a variant thereof that comprises a sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, or at least 150 identical contiguous amino acid residues of SEQ ID NO: 1, SEQ ID NO: 2, or SEQ ID NO: 3.

In some embodiments, the polypeptide comprises a sequence selected from the group consisting of SEQ ID NO: 1, SEQ ID NO: 2, and SEQ ID NO: 3, or a variant thereof that comprises up to 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, or 50 amino acid changes compared to SEQ ID NO: 1, SEQ ID NO: 2, or SEQ ID NO: 3.

In a particular embodiment of the first aspect, optionally in combination with any of the embodiments provided above or below, the polypeptide is chemically modified. In a more particular embodiment, the chemical modification comprises covalent modification of an amino acid. In another embodiment, the covalent modification is selected from the group consisting of methylation, acetylation, phosphorylation, ubiquitination, sumoylation, citrullination, ADP ribosylation, and combinations thereof. It belongs to the common general knowledge of the skilled person how to chemically modify the polypeptide using routine methods.

In a particular embodiment of the first aspect, optionally in combination with any of the embodiments provided above or below, the polypeptide further comprises a tag, particularly a tag suitable for detection and/or purification located at the N-terminus and/or at the C-terminus.

The term "tag", as used herein, refers to any amino acid sequence for which specific binding molecules are available, thus allowing the detection/purification of any polypeptide carrying said tag. The tag is generally placed at the amino- or the carboxyl-terminus of the polypeptide. The presence of such tag allows the adapter molecule to be detected using an antibody against the tag polypeptide. Also, the provision of the tag enables the adapter polypeptide to be readily purified by affinity purification using an anti-tag antibody or another type of affinity reagent that binds to the epitope tag. It should be understood that the skilled person would readily identify the tag suitable for the detection or purification using the tags available in the art.

The skilled person knows how to produce the polypeptides of the invention by routine methods well known in the art, for example, by chemical synthesis or by recombinant expression techniques, without exercising any inventive skill.

In a second aspect the invention provides an antibody that specifically binds to a polypeptide comprising or consisting of a sequence selected from the group consisting of SEQ ID NO: 1, SEQ ID NO: 2, and SEQ ID NO: 3. Examples of antibodies include, but are not limited to monoclonal antibodies, polyclonal antibodies, antibody fragments, antibody derivatives, Fab fragments, Fab' fragments, F(ab)2 fragments, Fd fragments, Fv fragments, single-chain Fv fragments (scFv), diabodies, tribodies, tetrabodies, dimers, trimers, and minibodies. In a particular embodiment of the second aspect, the antibody is a monoclonal antibody. The antibodies can be produced by any method known in the art for the generation of antibodies, in particular, by chemical synthesis or by recombinant expression techniques. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in WO2009100309.

As mentioned above, in a third aspect, the invention provides a nucleic acid which encodes the polypeptide as defined in the first aspect. In a particular embodiment of the third aspect, the nucleic acid is DNA or RNA.

As above mentioned, in a fourth and fifth aspects the invention provides a gene construct and an expression vector. Examples of suitable expression promoters and expression vectors include those conventionally used in molecular biology and known to the skilled person. The invention also provides, in a sixth aspect, host cell. Examples of suitable host cells and culture conditions include those conventionally used in cell biology and known to the skilled person.

As disclosed above, in a seventh aspect the invention also provides a process for producing the polypeptide of the invention. Of course, the specific conditions of cell culturing, polypeptide recovery and purification as well as other such assay conditions can be varied, depending on various factors including the host cell type and the like. Those skilled in the art will be able to determine operative and optimal assay conditions for producing the polypeptide by employing routine experimentation.

The invention also provides in a ninth aspect a process for amplifying a nucleic acid that comprises the step of contacting the nucleic acid with the polypeptide of the invention, and optionally, a DNA polymerase, particularly a strand-displacement polymerase, under conditions suitable for amplifying the nucleic acid. It should be understood that the skilled person would readily be able to identify the conditions suitable for amplifying the nucleic acid using any of the well stablished techniques known in the art. This information is commonly available and forms part of the general knowledge of the skilled person.

Notably, the polypeptide of the invention can be used for only priming the amplification or for the whole amplification process (i.e., priming and strand elongation). When used only for priming, the polypeptide is used in combination with a DNA polymerase, such as Phi29 polymerase. As used herein, the term "priming" refers to the generation of an oligonucleotide primer on a nucleic acid template by the polypeptide of the invention.

The term "nucleic acid", as used herein, relates to a deoxyribonucleotide or ribonucleotide polymer in either single or double stranded form and, unless otherwise limited, encompasses natural nucleotides and analogues of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid (PNA). A nucleotide is one monomer in an oligonucleotide or in a polynucleotide. A "nucleotide sequence" or "nucleic acid sequence" refers to the sequence of bases in an oligonucleotide or in a polynucleotide.

In a particular embodiment of the ninth aspect, optionally in combination with any of the embodiments provided above or below, the amplification process comprises the step of contacting the nucleic acid with a polypeptide of the invention and a Phi29 DNA polymerase under conditions suitable for amplifying the nucleic acid.

The term "strand-displacement DNA polymerase" refers to a DNA polymerase that performs a 3' end elongation reaction while removing a double-stranded portion of template DNA. Strand displacement DNA polymerases that can be used in the present invention may not be particularly limited, as long as they have strand-displacement activity, such as Phi29 DNA polymerase, and are compatible with the polypeptide of the invention. Depending on the thus selected polymerase type, the skilled in the art would know that the reaction conditions for a 3' end elongation reaction may be adequately set. As used herein, "Phi29 polymerase" or "Phi29 DNA polymerase" refers to the highly processive strand-displacement DNA polymerase from the bacteriophage Phi29 (i.e., ¢29). Phi29 polymerases can be obtained commercially (for example, from ThermoFisher, EP0091) and are readily available to the skilled person. The term "Phi29 polymerase" is also meant to encompass improved variants of the Phi29 polymerase, such as the chimeric Phi29 polymerase disclosed in the international application WO2011000997.

As used herein, the term "amplification" refers to one of the many ways in which a nucleic acid, in particular a DNA molecule, can be copied or multiplied. Non limiting examples for amplification methods include PCR (Polymerase Chain Reaction), LAMP (Loop mediated Isothermal Amplification), RDC (Reaction deplacement chimeric), NASBA (Nucleic Acid Sequence Based Amplification), or isothermal amplification, such as rolling circle amplification (RCA) or whole genome amplification (WGA).

Thus, in a particular embodiment of the ninth aspect, optionally in combination with any of the embodiments provided above or below, the amplification is selected from PCR (Polymerase Chain Reaction), LAMP (Loop mediated Isothermal Amplification), RDC (Reaction deplacement chimeric), NASBA (Nucleic Acid Sequence Based Amplification), rolling circle amplification (RCA), whole genome amplification (WGA), multiple displacement amplification (MDA), strand displacement amplification (SDA), and combinations thereof. In a more particular embodiment, the amplification is a combination of rolling circle amplification (RCA) and multiple displacement amplification (MDA).

In a particular embodiment of the ninth aspect, optionally in combination with any of the embodiments provided above or below, the nucleic acid is DNA, RNA, or a mixture thereof.

In a particular embodiment of the ninth aspect, optionally in combination with any of the embodiments provided above or below, the process comprises contacting the polypeptide of the invention and the DNA polymerase with the nucleic acid simultaneously or sequentially (i.e., first the polypeptide of the invention and then the strand-displacement DNA polymerase).

In a particular embodiment of the ninth aspect, optionally in combination with any of the embodiments provided above or below, the process further comprises contacting the nucleic acid with a buffer, magnesium chloride, nucleoside triphosphates. In a more particular embodiment, the nucleoside triphosphates are dCTP, dGTP, dTTP and dATP.

In a particular embodiment of the ninth aspect, optionally in combination with any of the embodiments provided above or below, the amplification is performed at a constant temperature from 25° C. to 60° C., particularly from 30° C. to 50° C., more particularly at about 50° C.

In a particular embodiment of the ninth aspect, optionally in combination with any of the embodiments provided above or below, the process further comprises at least one of the following steps: detecting the amplified nucleic acid; quantifying the amplified nucleic acid; sequencing the amplified nucleic acid; and processing the amplified nucleic acid, particularly, wherein the processing comprises digesting the amplified nucleic acid with at least one restriction enzyme. In a more particular embodiment, the process further comprises the step of digesting the amplified nucleic acid with at least one restriction enzyme. In a more particular embodiment, the process further comprises the step of digesting the amplified nucleic acid with at least one restriction enzyme and attaching single stranded hairpin adaptors to both ends of the digested nucleic acid thereby forming a closed linear DNA. In a more particular embodiment, the process further comprises the step of contacting the amplified nucleic with a protelomerase thereby forming a closed linear DNA. In a more particular embodiment, the process further comprises the step of sequencing the amplified nucleic acid and detecting one or a plurality of genetic variants in the sequenced, amplified nucleic acid. Methods of detecting, quantifying, sequencing, or processing nucleic acids are known to those skilled in the art and form part of the common general knowledge.

In a particular embodiment of the ninth aspect, optionally in combination with any of the embodiments provided above or below, the sequencing comprises fragmenting the amplified nucleic acid and attaching sequencing platform-specific adaptors to the fragmented nucleic acid. The skilled reader will routinely be able to optimize the fragmenting conditions and will know which adaptors to use depending on the sequencing platform to be used.

In a particular embodiment of the ninth aspect, optionally in combination with any of the embodiments provided above or below, sequencing is performed on selected sequences, exomes, transcriptome or whole genome.

As above explained, the invention also provides in a twelfth aspect a process for the production of a closed linear DNA using the polypeptide of the invention.

As used herein, the term "closed linear DNA" or "cIDNA" or "linear closed DNA" or "IcDNA" refers to a single stranded covalently closed DNA molecule that forms a "dumbbell" or "doggy-bone" shaped structure under conditions allowing nucleotide hybridization. Therefore, although the cIDNA is formed by a closed single stranded DNA molecule, the formation of the "dumbbell" structure by the hybridization of two complementary sequences within the same molecule generates a structure consisting on a double-stranded middle segment flanked by two single-stranded loops. The skilled in the art knows how to generate cIDNA from open or closed double stranded DNA—such as the amplified DNA produced in step (b)—using routine molecular biology techniques. For instance, the skilled in the art knows that a cIDNA can be generated by attaching single stranded hairpin adaptors—for instance, by the action of a ligase—to both ends of an open double stranded DNA. Another method known to the skilled in the art to generate closed linear DNA is through the action of a protelomerase on a double-stranded DNA that comprises at least two protelomerase target sequences.

In a particular embodiment of the twelfth aspect, optionally in combination with any of the embodiments provided above or below, the nucleic acid is a closed linear DNA.

In a particular embodiment of the twelfth aspect, optionally in combination with any of the embodiments provided above or below, the amplification performed in step (b) is a rolling-circle amplification (RCA).

The term "rolling-circle amplification" or "RCA" refers to nucleic acid amplification reactions involving the amplification of covalently closed DNA molecules, such as cIDNA or double stranded circular DNA, wherein a polymerase performs the extension of a primer around the closed DNA molecule. The polymerase displaces the hybridized copy and continues polynucleotide extension around the template to produce concatameric DNA comprising tandem units of the amplified DNA.

In a particular embodiment of the twelfth aspect, optionally in combination with any of the embodiments provided above or below, the amplification of step (b) is carried out with a strand-displacement DNA polymerase, particularly, a Phi29 polymerase.

In a particular embodiment of the twelfth aspect, optionally in combination with any of the embodiments provided above or below, the DNA template is selected from a closed linear DNA template or a circular double stranded DNA template.

In a particular embodiment of the twelfth aspect, optionally in combination with any of the embodiments provided above or below, the amplified DNA resulting from step (b) is a concatameric DNA comprising repeats of the DNA sequence of interest, wherein each one of the repeats is flanked by restriction sites and/or protelomerase target sequences.

In a particular embodiment of the twelfth aspect, optionally in combination with any of the embodiments provided above or below, the concatameric DNA comprises repeats of the DNA sequence of interest flanked by at least restriction sites, then step (c) is performed by: (c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments.

In a particular embodiment of the twelfth aspect, optionally in combination with any of the embodiments provided above or below, when the concatameric DNA comprises repeats of the DNA sequence of interest flanked by at least protelomerase target sequences, then step (c) is performed by contacting the concatameric DNA with a protelomerase, particularly, with TelN.

As used herein, "protelomerase" is any polypeptide capable of cleaving and rejoining a template comprising a protelomerase target site in order to produce a covalently closed linear DNA molecule. Thus, the protelomerase has DNA cleavage and ligation functions.

Enzymes having protelomerase-type activity have also been described as telomere resolvases (for example in *Borrelia burgdorferi*). A typical substrate for protelomerase is circular double stranded DNA. If this DNA contains a protelomerase target site, the enzyme can cut the DNA at this site and ligate the ends to create a linear double stranded covalently closed DNA molecule. The ability of a given polypeptide to catalyze the production of closed linear DNA from a template comprising a protelomerase target site can be determined using any suitable assay described in the art.

Examples of suitable protelomerases for use in the process of the invention include those from bacteriophages such as phiHAP-1 from *Halomonas aquamarina*, PY54 from *Yersinia* enterolytica, phiKO2 from *Klebsiella oxytoca* and VP882 from *Vibrio* sp., and N15 from *Escherichia coli* (TelN protelomerase), or variants of any thereof. Protelomerases, in particular TelN, can be obtained commercially or produced by routine methods.

In a further aspect, the invention provides a polypeptide comprising SEQ ID NO: 4 or a variant thereof at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 4. All embodiments and aspects above provided in relation to the polypeptides of the first aspect are also meant to apply to the polypeptide of this further aspect.

In one embodiment, the polypeptide comprises SEQ ID no: 4 or a variant thereof that comprises an amino acid sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, or at least 150 identical contiguous amino acid residues of SEQ ID NO: 4. In some embodiments, the polypeptide comprises SEQ ID no: 4 or a variant thereof that comprises 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more amino acid changes compared to SEQ ID NO: 4.

In particular, the invention also provides an antibody that specifically binds to a polypeptide comprising or consisting of sequence SEQ ID NO: 4; a nucleic acid sequence that encodes the polypeptide comprising SEQ ID NO: 4 or a variant thereof at least 80% identical, particularly at least 90% identical, to SEQ ID NO: 4, particularly, wherein the nucleic acid sequence is optimized for expression in a mammalian expression system, or alternatively, in a bacterial expression system; a gene construct comprising said nucleic acid sequence operatively linked to an expression promoter; an expression vector comprising said gene construct; a host cell comprising said nucleic acid sequence, said the gene construct, or said expression vector, a process for producing said polypeptide, process comprising the steps of a) culturing said host cell under conditions suitable for the production of the polypeptide; b) recovering the polypeptide; and, optionally, c) purifying the polypeptide; a polypeptide produced according to said process.

The invention also provides a process for amplifying a nucleic acid that comprises the step of contacting the nucleic acid with a polypeptide comprising SEQ ID NO: 4 or a variant thereof at least 80% identical, particularly at least 90% identical, to SEQ ID NO: 4, and, optionally, a DNA polymerase, particularly a strand-displacement DNA polymerase; under conditions suitable for amplifying the nucleic acid; the use of said polypeptide for amplifying, detecting, or sequencing a nucleic acid; the use of said polypeptide in combination with a strand-displacement DNA polymerase for amplifying, detecting, or sequencing a nucleic acid; a process for the production of a closed linear DNA comprising the steps of a) providing a DNA template comprising a DNA sequence of interest; b) amplifying DNA from the DNA template of step (a) wherein the amplification is primed with said polypeptide; c) generating a closed linear DNA with the amplified DNA produced in step (b); and d) optionally, purifying the generated closed linear DNA; the use of said polypeptide for the production of closed linear DNA; and a kit comprising (a) said polypeptide; (b) a strand-displacement DNA polymerase, particularly, a Phi29 polymerase; and (c) optionally, instructions for its use.

In a particular embodiment of this further aspect, optionally in combination with any of the embodiments provided above or below, the polypeptide consists of SEQ ID NO: 4 or a variant thereof at least 80%, at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 4.

In a particular embodiment of this further aspect, optionally in combination with any of the embodiments provided above or below, the variant thereof substantially maintains or improves the primase and polymerase activities.

In a particular embodiment of this further aspect, optionally in combination with any of the embodiments provided above or below, the polypeptide comprises primase and polymerase activities and, optionally, the sequence of the polypeptide is not 100% identical to the sequence of any extant polypeptide.

Throughout the description and claims the word "comprise" and variations of the word, are not intended to exclude other technical features, additives, components, or steps.

Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

The invention comprises the following embodiments:

1. Polypeptide comprising a sequence selected from the group consisting of SEQ ID NO: 1, SEQ ID NO: 2, and SEQ ID NO: 3, or a variant thereof at least 80% identical, particularly at least 90% identical, to SEQ ID NO: 1, SEQ ID NO: 2, or SEQ ID NO: 3.

2. Polypeptide comprising a sequence selected from the group consisting of SEQ ID NO: 1, SEQ ID NO: 2, SEQ ID NO: 3, and SEQ ID NO: 4, or a variant thereof at least 80% identical, particularly at least 90% identical, to SEQ ID NO: 1, SEQ ID NO: 2, SEQ ID NO: 3, or SEQ ID NO: 4.

3. The polypeptide according to any of embodiments 1-2, which comprises primase and polymerase activities.

4. The polypeptide according to any of embodiments 1-3, which comprises at least one improved property as compared to TthPrimPol.

5. The polypeptide according to embodiment 4, wherein the at least one improved property as compared to TthPrimPol is selected from greater pH stability, greater thermostability, greater primase activity, greater polymerase activity, greater fidelity, and greater expression rate.

6. The polypeptide according to any of embodiments 1-5, which comprises at least one of the following:

- a greater primase activity than TthPrimPol at a pH from 7.5 to 8.5, particularly at a pH of about 7.5;
- a greater polymerase activity than TthPrimPol at a pH from 7.5 to 8.5, particularly of about 7.5;
- a greater primase activity than TthPrimPol at a temperature of about 50° C.; or
- a greater polymerase activity than TthPrimPol at a temperature of about 50° C.

7. The polypeptide according to any of embodiments 5-6, wherein the primase or polymerase activity is measured by absorbance at a wavelength of 260 nm 8. The polypeptide according to any of embodiments 5-6, wherein the primase activity is measured by contacting the polypeptide and a strand-displacement DNA polymerase, particularly, a Phi29 polymerase, with a nucleic acid template under conditions suitable for amplifying the nucleic acid template and measuring the amplification products by absorbance at a wavelength of 260 nm.

9. The polypeptide according to any of embodiments 5-6, wherein the polymerase activity is measured by contacting the polypeptide with a nucleic acid template under conditions suitable for amplifying the nucleic acid template and measuring the amplification products by absorbance at a wavelength of 260 nm.

10. The polypeptide according to any of embodiments 5-9, wherein the fidelity is measured by next-generation sequencing.

11. The polypeptide according to any of embodiments 5-10, wherein the expression rate is measured by absorbance at a wavelength of 280 nm.

12. The polypeptide according to any of embodiments 1-11, wherein the variant thereof substantially maintains or improves the primase and polymerase activities.

13. The polypeptide according to any of embodiments 1-12, wherein the sequence of the polypeptide has an RMS value when aligned against the sequence of TthPrimPol of at least 2, at least 3, at least 4, or at least 5; optionally, wherein the RMS value is calculated with AlphaFold2, particularly, as explained in Example 9.

14. The polypeptide according to any of embodiments 1-13, wherein the sequence of the polypeptide is not 100% identical to the sequence of any extant polypeptide.

15. The polypeptide according to any of embodiments 1-14, which consists of a sequence selected from the group consisting of SEQ ID NO: 1, SEQ ID NO: 2, and SEQ ID NO: 3, or a variant thereof at least 80% identical, particularly at least 90% identical, to SEQ ID NO: 1, SEQ ID NO: 2, or SEQ ID NO: 3.

16. The polypeptide according to any of embodiments 1-15, wherein the variant thereof is at least 81%, at least 82%, at least 83%, at least 84%, at least 85%, at least 86%, at least 87%, at least 88%, at least 88.5%, at least 89%, at least 89.5%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5%, or at least 99.9% identical to SEQ ID NO: 1, SEQ ID NO: 2, or SEQ ID NO: 3.

17. The polypeptide according to any of embodiments 1-16, wherein the polypeptide is chemically modified, particularly, by a covalent modification of an amino acid selected from the group consisting of methylation, acetylation, phosphorylation, ubiquitination, sumoylation, citrullination, ADP ribosylation, and combinations thereof.

18. The polypeptide according to any of embodiments 1-17, further comprising a tag, particularly a tag suitable for detection and/or purification located at the N-terminus or at the C-terminus.

19. Antibody that specifically binds to a polypeptide comprising or consisting of a sequence selected from the group consisting of SEQ ID NO: 1, SEQ ID NO: 2, and SEQ ID NO: 3.

20. Nucleic acid sequence that encodes the polypeptide as defined in any of embodiments 1-18, particularly, wherein the nucleic acid sequence is optimized for expression in a mammalian expression system, or alternatively, in a bacterial expression system.

21. Gene construct comprising a nucleic acid sequence as defined in embodiment 20 operatively linked to an expression promoter.

22. Expression vector comprising the gene construct as defined in embodiment 21.

23. Host cell comprising the nucleic acid sequence as defined in embodiment 20, the gene construct as defined in embodiment 21, or the expression vector as defined in embodiment 22.

24. A process for producing the polypeptide as defined in any of embodiments 1-18, the process comprising the steps of:
- a) culturing the host cell as defined in embodiment 23 under conditions suitable for the production of the polypeptide;
- b) recovering the polypeptide; and,
- c) optionally, purifying the polypeptide.

25. A polypeptide obtainable by the process defined in embodiment 24.

26. A process for amplifying a nucleic acid that comprises the step of contacting the nucleic acid with a polypeptide as defined in any of embodiments 1-18, and optionally, a DNA polymerase, particularly a strand-displacement DNA polymerase; under conditions suitable for amplifying the nucleic acid.

27. A process for amplifying, detecting, or sequencing a nucleic acid that comprises the step of contacting the nucleic acid with a polypeptide as defined in any of embodiments 1-18, and optionally, a DNA polymerase, particularly a strand-displacement DNA polymerase; under conditions suitable for amplifying the nucleic acid.

28. The process according to any of embodiments 26-27, wherein the nucleic acid is DNA, RNA, or a mixture thereof.

29. The process according to any of embodiments 26-28, wherein the nucleic acid is a closed linear DNA.

30. The process according to any of embodiments 26-29, wherein the polypeptide as defined in any of embodiments 1-18 and the DNA polymerase are contacted with the nucleic acid simultaneously or sequentially.

31. The process according to any of embodiments 26-30, wherein the amplification is selected from PCR (Polymerase Chain Reaction), LAMP (Loop mediated Isothermal Amplification), RDC (Reaction deplacement chimeric), NASBA (Nucleic Acid Sequence Based Amplification), rolling circle amplification (RCA), whole genome amplification (WGA), multiple displacement amplification (MDA), strand displacement amplification (SDA), and combinations thereof; particularly, the amplification is a combination of rolling circle amplification (RCA) and multiple displacement amplification (MDA).

32. The process according to any of embodiments 26-31 further comprising at least one of the following steps:
- detecting the amplified nucleic acid;
- quantifying the amplified nucleic acid;
- sequencing the amplified nucleic acid; and
- processing the amplified nucleic acid, particularly, wherein the processing comprises digesting the amplified nucleic acid with at least one restriction enzyme.

33. The process according to embodiment 32, wherein sequencing comprises fragmenting the amplified nucleic acid and attaching sequencing platform-specific adaptors to the fragmented nucleic acid.

34. Use of a polypeptide as defined in any of embodiments 1-18 for amplifying, detecting, or sequencing a nucleic acid, particularly, wherein the nucleic acid is a closed linear DNA.

35. Use of a polypeptide as defined in any of embodiments 1-18 in combination with a DNA polymerase, particularly a strand-displacement DNA polymerase, for amplifying, detecting, or sequencing of a nucleic acid.

36. The use according to embodiment 35, wherein the strand-displacement DNA polymerase is a Phi29 DNA polymerase.

37. A process for the production of a closed linear DNA comprising the steps of:
- a) providing a DNA template comprising a DNA sequence of interest;
- b) amplifying DNA from the DNA template of step (a) wherein the amplification is primed with a polypeptide as defined in any of embodiments 1-18; and
- c) generating a closed linear DNA with the amplified DNA produced in step (b); and
- d) optionally, purifying the generated closed linear DNA.

38. The process according to embodiment 37, wherein the amplification performed in step (b) is a rolling-circle amplification.

39. The process according to any of embodiments 37-38, wherein the amplification of step (b) is carried out with a strand-displacement DNA polymerase, particularly, a phi29 polymerase.

40. The process according to any of embodiments 37-39, wherein the DNA template is selected from a closed linear DNA template or a circular double stranded DNA template.

41. The process according to any of embodiments 37-40, wherein the amplified DNA resulting from step (b) is a concatameric DNA comprising repeats of the DNA sequence of interest, wherein each one of the repeats is flanked by restriction sites and/or protelomerase target sequences.

42. The process according to embodiment 41, wherein when the concatameric DNA comprises repeats of the DNA sequence of interest flanked by at least restriction sites, then step (c) is performed by: (c.1) contacting the concatameric DNA with at least one restriction enzyme thereby producing a plurality of open double stranded DNA fragments each containing the DNA sequence of interest, and (c.2) attaching single stranded DNA adaptors to both ends of the open double stranded DNA fragments.

43. The process according to embodiment 41, wherein when the concatameric DNA comprises repeats of the DNA sequence of interest flanked by at least protelomerase target sequences, then step (c) is performed by contacting the concatameric DNA with a protelomerase, particularly, with TelN.

44. Use of a polypeptide as defined in any of embodiments 1-18 for the production of closed linear DNA.

45. A kit comprising:
- (a) a polypeptide as defined in any of embodiments 1-18;
- (b) a DNA polymerase, particularly a strand-displacement DNA polymerase; and
- (c) optionally, instructions for its use.

46. The kit according to embodiment 45, further comprising one or more deoxyribonucleoside triphosphates.

47. The kit according to any of embodiments 45-46, wherein the strand-displacement DNA polymerase is a Phi29 DNA polymerase.

EXAMPLES

Example 1: Materials and Methods

Production and Purification of Synthetic PrimPols of the Invention

Synthetic PrimPols of SEQ ID NO: 1, 2, 3, and 4 were codon optimized for expression in *E. coli* and synthesized into pET28 expression vector (Merk) and transformed into *E. coli* BL21 (DE3) (Life Technologies) strain for protein expression following standard procedures. Briefly, cells were incubated in LB medium (Thermofisher) at 37° C. until OD reached Abs600 nm of 0.6 and induced with 1 mM IPTG. After induction, cells were incubated overnight at 18° C. and cells were cultured by centrifugation at 4000 rpm for 15 minutes. Pellets were resuspended in extraction buffer (50 mM Tris-HCl pH 7.5, 5% glycerol, 0.5 mM EDTA and 1 mM dithiothreitol (DTT)) and 1M NaCl, 0.25% Tween-20 and 30 mM imidazole. To resuspended pellets 1 vial of protease inhibitor cocktail and100 mg/ml of lysozyme were added and incubated at 4° C. for 15 minutes. Then the pellet was sonicated for 3 cycles of 10 minutes at 30% amplitude. Ultracentrifugation at 33000 G for 1 hour was performed for the separation of the cell debris. The supernatants were filtered and mixed with His GraviTrap affinity column (GE Healthcare) pre-washed with extraction buffer according to manufacturer's instructions. Protein was eluted using extraction buffer with 500 mM imidazole and 1M NaCl. Appropriate fractions were collected and diluted with extraction buffer lacking NaCl and loaded onto a HiTrap Heparin HP column (5 ml, GE Healthcare). The column was eluted with a linear gradient extraction buffer with 0.1 to 1M. NaCl. Verification of the protein purification was done by sodium dodecyl sulfate-polyacrylamide gel electrophoresis (SDS-PAGE) 12% acrylamide following standard procedures. Protein concentration was calculated by measuring the absorbance at 280 nm in Nanodrop 2000C following manufacturer's instructions.

Primase Activity Assay

Primase activity assays were carried out in reactions containing, per 12.5 μL reaction volume: 30 mM Tris-HCl, 30 mM KCl, 7.5 mM $MgCl_2$, 2 mM DTT, 0.5 mM dNTP, 400 nM primase-polymerase and 100 ng of a single stranded DNA template (M13mp18) (New England Biolab). Reactions were incubated at 30 or 50° C. at the reaction times indicated, and pH 7 and 8. Reactions were stopped by incubation at 65° C. for 15 min. Samples were then loaded into a 2% agarose gel for electrophoretic analysis and measured by Nanodrop2000C following manufacturer's instructions.

Polymerase Activity Assay

For polymerase activity assays extension of a gapped plasmid was performed. psJ4 plasmid was obtained by the introduction of Nb.Bpu101 and Nt.Bpu10l nickase enzyme restriction sites upstream and 64 bp downstream of the transcription initiation site of the lacZa gene, using pUC19 plasmid (Thermofisher) as base. Plasmid was assembled by Gibson assembly in the following manner: a 566 bp DNA string containing the lacZa gene with the desired mutations was purchased from GeneArt (ThermoFischer). pUC19 was amplified by PCR using primer 1 of sequence CAGCTCACTCAAAGGCGGTA (SEQ ID NO: 5) and primer 2 of sequence TCTGCTCTGATGCCGCATAG (SEQ ID NO: 6). Both fragments were assembled by Gibson assembly using Gibson Assembly HiFi kit (GeneArt), transformed into the provided competent cells and plated onto x-gal, IPTG and carbenicillin containing LB agar plates. Colonies containing the correct psJ4 plasmid were checked by double strand digestion with both Nb.Bpu101 and Nt. Bpu101 restriction enzymes. Gapped plasmid was obtained by digestion with either Nb.Bpu101 or Nt.Bpu101 restriction enzyme and incubation with a 64 bp single stranded competitor during three heat/cool cycles of 95° C. for 1 min, 60° C. for 10 min, and 37° C. for 20 min. Gapped plasmid was further purified using a 100 kDa cutoff Amicon Ultrafilter (Millipore).

Gapped plasmid extension assay was performed in reactions containing, per 12.5 μL reaction volume: 30 mM Tris-HCl, 30 mM KCl, 7.5 mM $MgCl_2$, 5 mM $(NH_4)$ $2SO_4$, 2 mM DTT, 0.5 mM dNTP, 100 nM primase-polymerase and 35 ng of gapped plasmid. Reactions were incubated at 30 C for 30 minutes and loaded into a 1% agarose gel for electrophoretic analysis.

Fidelity Assay

For fidelity assay, a modified version of the plasmid pUC18 named pSJ4 was used. pSJ4 contained two endonuclease nicking sites (Nb.Bpu101 and Nt.Bpu101) at −6 and +58 of the lacza gene. Gapped plasmids were generated and fidelity assay was conducted as described by (Guilliam T A, et at., "Human PrimPol is a highly error-prone polymerase regulated by single-stranded DNA binding proteins", Nucleic Acids Res, 2015 January, vol 43 (2), pp. 1056-68).

Closed Linear DNA Template Generation

Closed linear DNA (clDNA) was produced by processing plasmidic DNA by TelN as described in Heinrich J. et al., "Linear closed mini DNA generated by the prokaryotic cleaving-joining enzyme TelN is functional in mammalian cells", J Mol Med, 2002, vol. 80 (10), pp. 648-54. The processed plasmids contained the gen of interest flaked by TelN recognition sites. Digested lcDNA was purified from an agarose gel and used as templated for RCA reactions.

Rolling Circle Amplification Reactions

Rolling circle amplification reactions (RCA) were carried by denaturing template DNA (1.25 ul) with a 3-minute incubation with 1.25 ul 0.1M NaOH, Denaturation was neutralized by addition of reaction buffer 1.25 ul (Buffer A 10X: 500 mM TrisHCl, 500 mM KCl, 100 mM MgCl2. 10 mM DTT, 1 mg/mL BSA, 5 mM dNTPs; or Buffer B 10X: 300 mM Tris-HCl, 300 mM KCl, 75 mM $MgCl_2$, 5 mM $(NH_4)$ $2SO_4$, 20 mM DTT, 5 mM dNTPs; buffers adjusted at stated pH). The primase-polymerase and Phi29 DNA polymerase were added at the concentrations indicated. Reactions were incubated for 3 hours at 30° C. unless otherwise indicated.

Next Generation Sequence of RCA

Concatemers from RCA synthesized by each primase-polymerase together with Phi29 DNA polymerase were analyzed by NGS. clDNA carrying the luciferase gen was used as templated. RCA concatamers were fragment by sonication and fragments were sequence by Illumina following standard procedures. All reads containing the exact sequence were mapped to the reference template. Reads were count and the percentage of mapped reads were calculated. DNA amplified by PCR by Phusion High Fidelity Polymerase (NEB) was used as control.

TelN Digestion

TelN digestion of RCA product was carried out on 100 ng of RCA product as described in Heinrich supra. Briefly, 1 ul TelN enzyme (NEB), 2 ul ThermoPol Reaction Buffer (10X) and up to 20 μl of nuclease free water. The mixture was incubated at 30° C. for 30 minutes and loaded into a 1% agarose gel for DNA electrophoresis analysis.

Example 2: Synthetic PrimPols have Higher Expression and Purification Yields

Synthetic PrimPol 1 (SEQ ID NO: 1), PrimPol 2 (SEQ ID NO: 4), PrimPol 3 (SEQ ID NO: 3), and PrimPol 4 (SEQ ID NO: 4), and TthPrimPol were expressed in pET-28a plasmid in *E. coli* BL21 DE3 cells (Thermofisher) following standard procedures. OD600 0.6 Induction by IPTG (1 mM) was carried out overnight at 18° C.

Briefly, pelleted cells frozen at −20 C were thawed in 50 mM Tris-HCl PH 7.5, 5% glycerol, 0.5 mM EDTA, 1 mM DTT, 2M NaCl, 0.25% Tween-20 and 30 mM imidazole and sonicated. After centrifugation at 40000 g, the supernatant was added to HisTrap Nickel resin (Ni-NTA) and incubated for 1 h. The resin was washed three times with the buffer mentioned above and eluted with the same buffer but containing 500 mM 4rotelome, in 1 mL fractions. Fractions were collected and passed through a HiTrap Heparing HP column according to manufacturer's instructions. Samples were eluted with a salt concentrated buffer (50 mM Tris-HCl pH 7.5, 5% glycerol, 0.5 mM EDTA, 1 mM DTT, 1M NaCl). The samples contained purified primase-polymerase enzymes.

Expression tests for synthetic primase-polymerases and TthPrimPol are shown in FIG. 1. As shown in this Figure, synthetic PrimPols 1~4 of the invention present a higher expression rate than TthPrimPol. This was particularly remarkable for PrimPol 4 (SEQ ID NO: 2), which reached production yields up to 50% higher than those of TthPrimPol.

Figure 2:
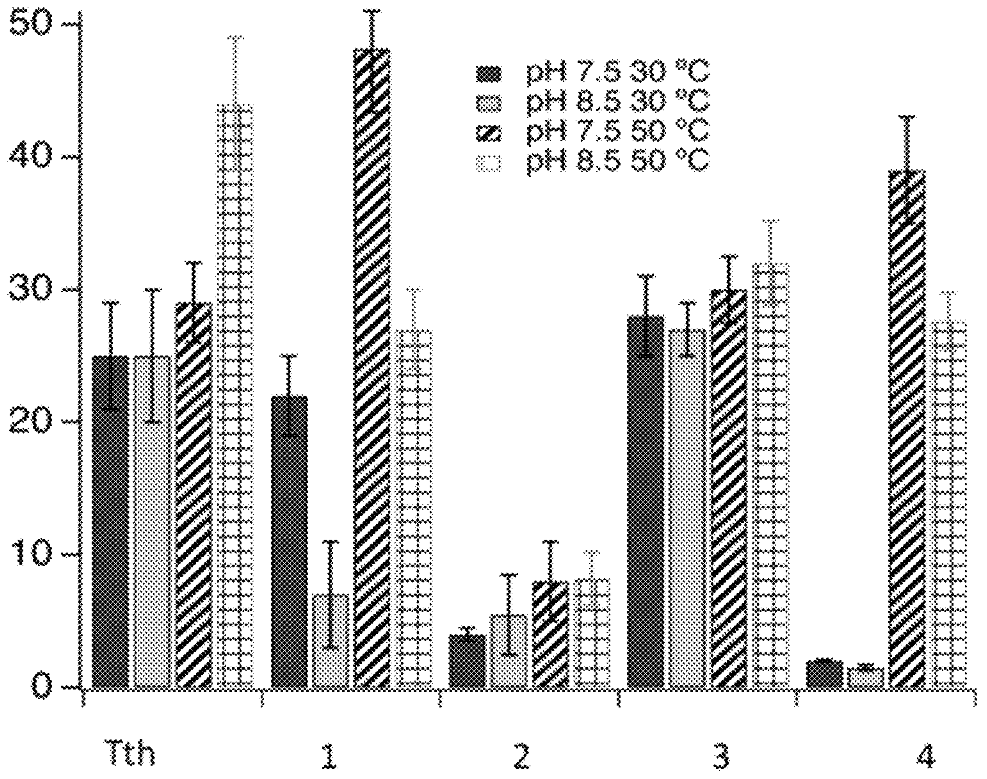
FIG. 2, related to Example 3, shows the priming efficiency of a circular ssDNA template by synthetic PrimPols and TthPrimPol under different conditions. The y-axis represents the total DNA concentration (ng) produced in the priming reaction with the indicated PrimPol. "Tth" refers to TthPrimPol, "1" refers to PrimPol 1 of SEQ ID NO:1, "2" refers to PrimPol 2 of SEQ ID NO:4, "3" refers to PrimPol 3 of SEQ ID NO:3, "4" refers to PrimPol 4 of SEQ ID NO: 2.

Example 3: Synthetic PrimPols Provide Higher Priming Activity Under Some Conditions Primase-polymerase activity in the presence of $Mg^{2+}$ as a cofactor is an important feature of PrimPols. For RCA applications, the presence of $Mg^{2+}$ as a cofactor, instead of $Mn^{2+}$ needed by most known primases, is crucial to maintain the high fidelity of the Phi29 DNA polymerase used for subsequent DNA synthesis. To test whether synthetic PrimPols retained primase-polymerase activity in the presence of $Mg^{2+}$, their priming activity was assayed on M13mp18 ssDNA. As shown in FIG. 2, all synthetic PrimPols were able to generate primers in the presence of M13mp18 ssDNA template, dNTPs and $Mg^{2+}$, whereas no primers were obtained in the absence of dNTPs. Reactions were incubated at 30° C. or 50° C. and at 7.5 or 8.5 pH for 6 hours. The assays were carried out with M13mp18 ssDNA as substrate and 200 nM of each enzyme. All enzymes showed higher activity at 50° C.

In the case of pH activity, TthPrimPol showed higher primase activity at pH 8.5 only at 50° C., contrary to PrimPol 1 and PrimPol 4, which have higher activity at pH 7.5 at 50° C. PrimPol 2 and PrimPol 3 activity showed similar priming activity at both pH values. Reactions were incubated for 6 hours at different conditions and stopped at 65° C.

In summary, these results show that synthetic PrimPol 1 and PrimPol 4 have a higher primase activity than TthPrimPol at lower pH and higher temperatures. Synthetic PrimPol 3 provides priming efficiencies similar to TthPrimPol under most conditions.

Example 4: Synthetic PrimPols Provide High Sequence Fidelity

Figure 3:
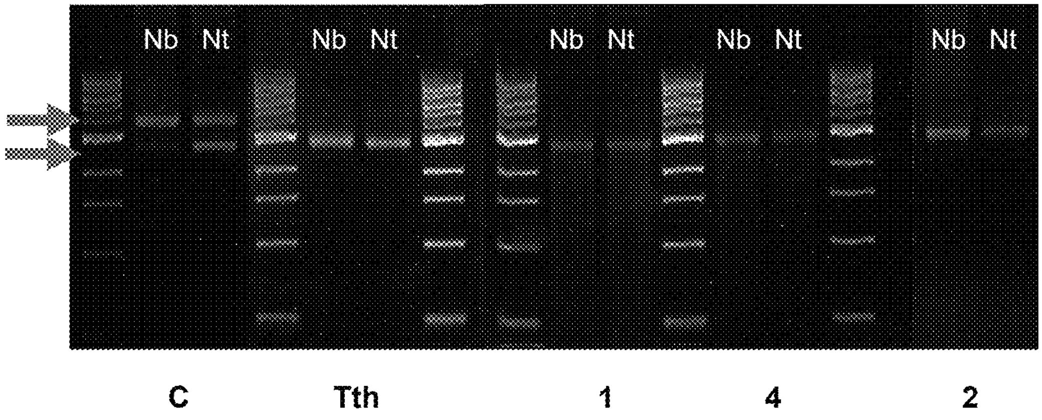
FIG. 3, related to Example 4, shows gapped plasmid extension assay based on the psJ4 plasmid. A gapped plasmid was generated with a gap in the 5'-3' strand (Nb) or 3'-5' strand (Nt). When the gap was present, EcoRI could completely cleave the plasmid, when the gapped was filled by a polymerase, EcoRI regained the ability to completely cleave the plasmid. Reactions were carried out with 100 nM of stated primase polymerase and 35 ng of gapped plasmid in the presence of $Mg^{2+}$ and dNTPs, for 30 minutes at 30° C. Reaction product and gapped plasmid substrate, as control, were subsequently digested with EcoRI at 37° C. for 15 minutes and loaded into a 1% agarose gel. The presence of digested linear plasmid and the absence of gapped plasmid indicates that primase polymerases are able to extend the gapped substrate. The upper arrow indicates gapped, the lower arrow indicates linear. "C" refers to control, "Tth" refers to TthPrimPol, "1" refers to PrimPol 1 of SEQ ID NO:1, "2" refers to PrimPol 2 of SEQ ID NO:4, and "4" refers to PrimPol 4 of SEQ ID NO:2.

To assess the polymerase activity of the synthetic primase polymerases, it was first tested whether they could complete the polymerization of a gapped plasmid as explained above in Example 1. As shown in FIG. 3, synthetic PrimPols were able to extend the 64 bp gapped plasmid, which allowed for complete cleavage with EcoRI, confirming the DNA polymerization activity of synthetic PrimPols of the invention.

Also, RCA reactions were carried out as explained above in Example 1, and the amplification products were then sequenced by NGS. Concatemers produced by all PrimPols in combination with Phi29 polymerase were fragmented by sonication and sequenced to check the fidelity of the amplification using as template DNA carrying a luciferase gene. PCR product of the plasmid substrate was used as control of the sequencing error. All reads obtained after the experiment were mapped using the reference sequence of the substrate and a similar percentage of mapped reads were obtained with all enzyme combinations. The sequencing results are provided in Table 2 below:

TABLE 2

| Sample | mapped | Total reads | % mapped reads | % no mapped reads | Normalized mapped on *T. Thermophilus* |
|---|---|---|---|---|---|
| PCR | 289000 | 306591 | 94.26 | 5.74 | |
| *T. Thermophilus* | 206184 | 276761 | 74.50 | 25.50 | 1 |
| PrimPol 1 | 190070 | 241627 | 78.66 | 21.34 | 1.05 |
| PrimPol 2 | 189187 | 252834 | 74.83 | 25.17 | 1 |
| PrimPol 3 | 192000 | 252834 | 75.94 | 24.06 | 1.02 |
| PrimPol 4 | 187676 | 273448 | 68.63 | 31.37 | 0.92 |

These results show that PrimPol 1 (SEQ ID NO: 1) and PrimPol 3 (SEQ ID NO: 3) provide an amplification fidelity even higher than TthPrimPol.

Example 5: Synthetic PrimPols have Priming Activity at 30° C.

The ability of the synthetic PrimPols to synthesize primers that Phi29 DNA polymerase can subsequently elongate to generate long concatemers in high yields was measured as disclosed above in Example 1 (RCA amplification). Reactions comprised, for a 12.5 ul reaction, 250 ng of PrimPol, 210 ng of Phi29 DNA polymerase, 0.5 mM dNTPs, 10 mM $MgCl_2$. Reactions were carried out for 3 hours at 30° C. and inactivated at 65° C. for 10 minutes.

Figure 4:
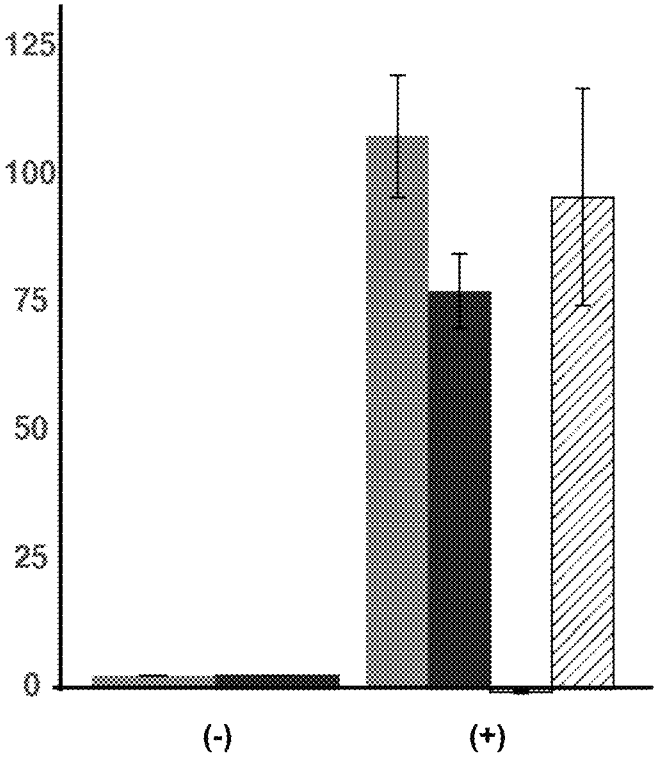
FIG. 4, related to Example 5, shows a quantification of the amplification of a clDNA template with the indicated PrimPol in combination with Phi29 DNA polymerase at low temperatures (30° C.). The y-axis represents the amount of amplified DNA (ng/μl). In the left group (−) the reaction was carried out in the absence of Phi29, and in the right group (+) the reaction was carried out in the present of Phi29. Within each group, the first column from the left represents TthPrimPol, the second represents PrimPol 1 of SEQ ID NO:1, the third represents a negative control without any PrimPol, and the fourth represents PrimPol 4 of SEQ ID NO:2.

As shown in FIG. 4, both PrimPol 1 and PrimPol 4 showed a capacity equivalent to TthPrimPol to synthesize primers that are later elongated by Phi29 DNA pol at low temperature (i.e., 30° C.).

Example 6: Synthetic PrimPols have Improved Priming Activity at 50° C.

For the application of PrimPols to industrial-scale settings, a desirable feature of these enzymes is their ability to tolerate and produce high DNA yields under the expected reaction condition variability on industrial processes. The ability of the synthetic PrimPols to synthesize primers at higher temperatures was measured as disclosed above.

Figure 5:
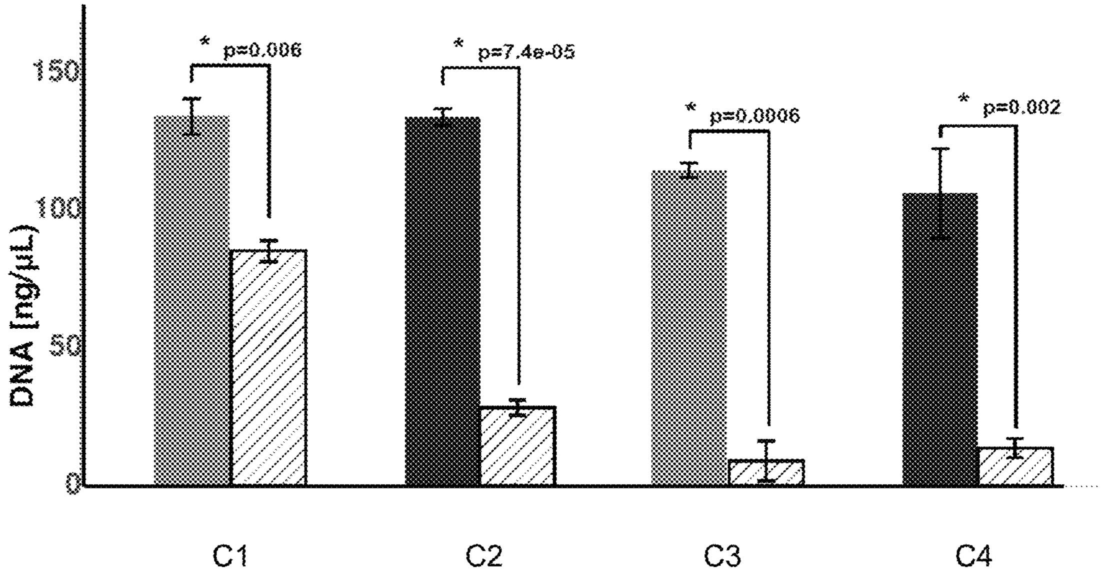
FIG. 5, related to Example 6, shows a quantification of the amplification of a clDNA template with the indicated PrimPol in combination with Phi29 DNA polymerase at high temperatures (50° C.). The y-axis represents the amount of amplified DNA (ng/μl). The conditions tested were the following: "C1", pH 8.5, 50 nM PrimPol, 25 ng/μl Phi29, 0.5 ng/μl DNA template; "C2", pH 7.5, 600 nM PrimPol, 25 ng/μl Phi29, 0.5 ng/μl DNA template; "C3", pH 7.5, 50 nM PrimPol, 8 ng/μl Phi29, 0.1 ng/μl DNA template; "C4", pH 8, 325 nM PrimPol, 16.5 ng/μl Phi29, 0.3 ng/μl DNA template. Grey bars represent PrimPol 1 of SEQ ID NO:1; black bars represent PrimPol 2 of SEQ ID NO:4, and bars with diagonal stripes represent TthPrimPol. P-values were calculated by pairwise t-test.

As shown in FIG. 5, synthetic PrimPol 1 (SEQ ID NO: 1) and PrimPol 4 (SEQ ID NO: 2) were able to generate higher amplification yields than TthPrimPol under various conditions, and higher yields even when compared to the optimal working conditions of TthPrimPol (i.e., pH 8.5).

These results clearly show that synthetic PrimPols of the invention provide more efficient priming than TthPrimPol under various conditions, which make them highly suitable for use in industrial settings.

Example 7: Synthetic PrimPols are Faster than Known PrimPols

The priming speed of synthetic PrimPol 1 (SEQ ID NO: 1) and PrimPol 3 (SEQ ID NO: 3) was compared to that of TthPrimPol.

PrimPols were incubated under the same conditions to test the rolling circle amplification activity in combination with Phi29 polymerase. 0.5 ng/ul of double stranded clDNA carrying luciferase gene were incubated with 200 nM PrimPol and 20 nM Phi29 DNA polymerase at pH 7.5 and 30° C. for 3 and 6 hours. Reactions were stopped at 65° C. for 15 min. DNA concentration was measured by fluorescence with picoGreen reagent.

Figure 6:
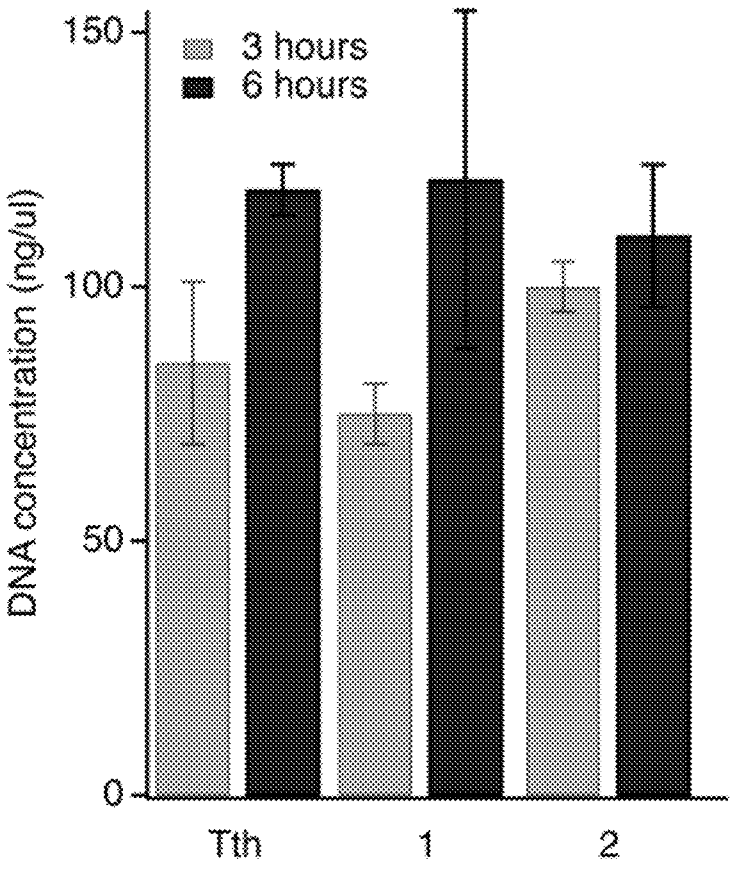
FIG. 6, related to Example 7, shows a quantification of the amplification products of reactions carried out with the indicated PrimPol in combination with Phi29 DNA polymerase at different reaction times: 3 and 6 hours. The y-axis represents the amount of amplified DNA (ng/μl). "Tth" refers to TthPrimPol, "1" refers to PrimPol 1 of SEQ ID NO:1, and "2" refers to PrimPol 3 of SEQ ID NO:3.

As shown in FIG. 6, at these conditions synthetic PrimPol 1 and TthPrimPol produced DNA at similar speed when combined with Phi29. However, PrimPol 3 produced higher concentration of amplified DNA faster than TthPrimPol (3 hours). Two replicates per experiments were carried out.

Example 8: Production of clDNA with Synthetic PrimPols

Yield is a very important factor when producing clDNA by RCA amplification. However, high quality of the amplified DNA is an essential requirement of the process. The capacity of synthetic PrimPol 1 and PrimPol 4 for producing high quality clDNA was tested as explained in Example 1.

Figure 7:
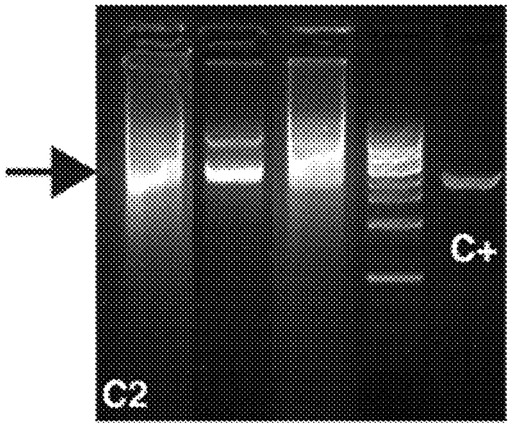
FIG. 7, related to Example 8, shows an agarose gel loaded with the clDNA produced by RCA amplification primed with the indicated PrimPol, followed by TelN processing. Arrow indicates the band corresponding the clDNA product. "Tth" refers to TthPrimPol, "1" refers to PrimPol 1 of SEQ ID NO:1, "4" refers to PrimPol 4 of SEQ ID NO:2, "C+" refers to the ClDNA template used for the amplification.

FIG. 7 shows that synthetic PrimPols 1 (SEQ ID NO: 1) and 4 (SEQ ID NO: 2) were able to prime a clDNA for synthesizing concatemers that could be then processed with TelN, thereby generating clDNA equal to the original template.

Example 9: Protein Structure Prediction Using Alphafold2

The AlphaFold2 models were calculated on the Alphfold2 online platform (https://colab.research.google.com/github/sokrypton/ColabFold/blob/main/AlphaFold2.ipyn b). The default parameters were used estimating 5 models. Visualization of the best resulting models was performed with PyMol (The PyMOL Molecular Graphics System, Version 2.0 Schrödinger, LLC.). Four structures were predicted: TthPrimPol, PrimPol 1 (SEQ ID NO: 1), PrimPol 3 (SEQ ID NO: 3), and PrimPol 4 (SEQ ID NO: 2). The three synthetic enzymes (PrimPol 1, 3 and 4) were aligned against TthPrimPol and RMS (root-mean-square) values were estimated.

The alignment of TthPrimPol versus PrimPol 4 (SEQ ID NO: 2) resulted in an RMS value of 5.6. Any value about 2 means a significant structural deviation.

The structure was divided into two subdomains, with clear displacement in the C-terminal subdomain. The N-terminal subdomain contains the catalytic residues and metal binding core, being the catalytic domain. The most significant displacement lied on the C-terminal subdomain that is involved in the binding and initiating of 5'NTP throughout a PriCT-1 motif. This binding domain is crucial for the enzyme to act as a primase The structural alignment of TthPrimPol versus PrimPol 1 (SEQ ID NO: 1) resulted in an RMS value of 7.6. Finally, the structural alignment of TthPrimPol versus PrimPol 3 (SEQ ID NO: 3) yielded an RMS value of 5.8.

Overall, these results suggest that the synthetic PrimPols 1, 3 and 4 maintain the catalytic activity throughout a very similar catalytic subdomain at the N-terminal but have a significantly displaced binding subdomain at the C-terminal as comparted to TthPrimPol.

CITATION LIST

WO2009100309

WO2011000997

Altschul et al., "Basic local alignment search tool", 1990, J. Mol. Biol, v. 215, pages 403-410.

Guilliam T A, et at., "Human PrimPol is a highly error-prone polymerase regulated by single-stranded DNA binding proteins", Nucleic Acids Res, 2015 January, vol 43 (2), pp. 1056-68.

Heinrich J. et al., "Linear closed mini DNA generated by the prokaryotic cleaving-joining enzyme TelN is functional in mammalian cells", J Mol Med, 2002, vol. 80 (10), pp. 648-54.

The invention claimed is:

1. A polypeptide comprising the sequence of SEQ ID NO: 1, or a variant thereof at least 90% identical to SEQ ID NO: 1.

2. The polypeptide according to claim 1, wherein the polypeptide comprises primase and polymerase activities.

3. The polypeptide according to claim 1, wherein the polypeptide comprises at least one improved property as compared to TthPrimPol selected from the group consisting of greater primase activity, greater polymerase activity, greater fidelity, greater pH stability, greater thermostability, and greater expression rate.

4. The polypeptide according to claim 1, which consists of the sequence of SEQ ID NO: 1.

5. The polypeptide according to claim 2, wherein the variant thereof is identical to SEQ ID NO: 1 and substantially maintains or improves the primase and polymerase activities.

6. The polypeptide according to claim 1, further comprising a tag.

7. Nucleic acid sequence that encodes the polypeptide as defined in claim 1.

8. A process for amplifying a nucleic acid that comprises the step of contacting the nucleic acid with:

a polypeptide as defined in claim 1; and a DNA polymerase.

9. The process according to claim 8, further comprising at least one step selected from the group consisting of:

detecting the amplified nucleic acid;

quantifying the amplified nucleic acid;

sequencing the amplified nucleic acid; and processing the amplified nucleic acid.

10. The process according to claim 8, wherein the nucleic acid is a closed linear DNA.

11. The polypeptide according to claim 6, wherein the tag is a tag suitable for detection or purification and is located at the N-terminus or at the C-terminus of the polypeptide.

12. The process according to claim 8, wherein the DNA polymerase is a strand displacement DNA polymerase.

13. The process according to claim 12, wherein the strand displacement DNA polymerase is a Phi29 polymerase.

14. The process according to claim 9, wherein the processing comprises digesting the amplified nucleic acid with at least one restriction enzyme.

15. The process according to claim 9, wherein the processing comprises digesting the amplified nucleic acid with at least one restriction enzyme and attaching adaptors to the digested nucleic acid.

16. The process according to claim 9, wherein the processing comprises contacting the amplified nucleic with a protelomerase thereby forming a closed linear DNA.

* * * * *

SEQUENCE LISTING

```
Sequence total quantity: 6
SEQ ID NO: 1            moltype = AA  length = 298
FEATURE                 Location/Qualifiers
source                  1..298
                        mol_type = protein
                        organism = synthetic construct
SEQUENCE: 1
RAPHSSPLEA ALGYARLGYP VLPLLPGEKR PHPRLVPHGL KEASQDPATL EAWWRSCPEA  60
GVGILAPAGV LVLDFDDPTA WEGLRQEHPA LEAAPRQRTP KGGVHVFLRL PEGVRLSASV  120
RAIPGVDLRG MGRAYVVAAP TRLKDGRTYS WEVPLVRPAE LPPVPEALLA RLLPPPPPPP  180
REVWTPVEGA SPKRLRALLE AYAHRVAATP PGTRHNTLIR YAVAAGGLIP HGLDPREAEE  240
ALVAAALSAG LPEREARAAV RWGLEVGRSR PLDLESSLPP RLPWTYRGRV YARVRRWA    298

SEQ ID NO: 2            moltype = AA  length = 298
FEATURE                 Location/Qualifiers
source                  1..298
                        mol_type = protein
```

-continued

```
                       organism = synthetic construct
SEQUENCE: 2
AHSTSPLEAA LGYARMGYPV LPVAPGSKRP HPRLVPHGLK EASTDPATIE AWWRSCPEAN  60
VGILAPEGVL VLDLDDPTAW EGLRQLHPAL LAAPRARTPR GGVHLYLRLP PGVRLSASVR  120
ALPGVDLRGM GRAYVVAAPS RLKDGRTYAW VVPLRRPSEL PPVPQALLAR LLAPPPPPAA  180
RPVSTPVEGA SPKRLRALLE AACHRVAHTP PGQRHNTLIR HAVAVGGLIP HGLDQEEAEE  240
ALVAAALSAG LPEREARAAV RWGLEAGASR PLVLKPSLPP RLRWTIRRRV RARGRRHG    298

SEQ ID NO: 3           moltype = AA  length = 298
FEATURE                Location/Qualifiers
source                 1..298
                       mol_type = protein
                       organism = synthetic construct
SEQUENCE: 3
ALSTSPLEAA LGYARMGYPV LPVAPGSKRP HPRLVRHGLK EATTDPALIE AWWSSRPEAN  60
VGILPPAGVL VLDLDSPAGW AGLRQLHPAL LAAPRARTPG GGVHLYFRLP PGVRLSASVR  120
VLPGVDLRGM GRAYVVAPPS RHADGRTYEW VVPLRRPSEL PPVPQALLAL LLAPPPPPAA  180
RPVSTPVASA RPKAYRAALE AECDRVARTP PGQRHNTLIR HAVALGGLIP RGLDQEEVEG  240
ALLAAALRAG LPEREARAAI RWGLEAGASR PLALKPRLPP RLRWTIRRRA RARGRRHG    298

SEQ ID NO: 4           moltype = AA  length = 298
FEATURE                Location/Qualifiers
source                 1..298
                       mol_type = protein
                       organism = synthetic construct
SEQUENCE: 4
ALSTSPLEAA LAYARMGYPV LPVAPGSKRP HPRLVRHGLK EATTDPAQIE AWWSRRPEAN  60
VGILTPSGVL VLDLDSPDGW AGLRQLHPAL LPAPKVRTPG GGVHLYFRLP PGVRLRASVR  120
VLPGIDLRGM GRAYVVAPPS RHAHGRTYEW VVPLRAPSEL PPVPQALLAL LLAPPPPPAA  180
RPVSPPVASA RPDAYRAALE AECDRVARTP PGQRHNTLIR HAVALGGLVP RGLDEEEVEG  240
ALLAAALRAG LAEREARATI RWGLEAGASR PLDLRPRLPP RLRWRIRRRA RARGRRHG    298

SEQ ID NO: 5           moltype = DNA  length = 20
FEATURE                Location/Qualifiers
source                 1..20
                       mol_type = other DNA
                       organism = synthetic construct
SEQUENCE: 5
cagctcactc aaaggcggta                                              20

SEQ ID NO: 6           moltype = DNA  length = 20
FEATURE                Location/Qualifiers
source                 1..20
                       mol_type = other DNA
                       organism = synthetic construct
SEQUENCE: 6
tctgctctga tgccgcatag                                              20
```